US011207338B2

(12) United States Patent
Huh et al.

(10) Patent No.: US 11,207,338 B2
(45) Date of Patent: Dec. 28, 2021

(54) COMPOSITION FOR PREVENTING AND TREATING OSTEOPOROSIS, COMPRISING DIHYDROPHASEIC ACID 3'-O-β-D-GLUCOPYRANOSIDE ISOLATED FROM LYCIUM ROOT BARK EXTRACTS

(71) Applicant: DONG WOO DANG CO., LTD, Yeongcheon-si (KR)

(72) Inventors: Dam Huh, Daegu (KR); Seon-Yong Jeong, Yongin-si (KR); Eunkuk Park, Suwon-si (KR); Moon-chang Kim, Suwon-si (KR); Ji Won Lee, Gyeongsan-si (KR); Jeong Hyun Kim, Suwon-si (KR)

(73) Assignee: DONG WOO DANG CO., LTD, Yeongcheon-si (KR)

( * ) Notice: Subject to any disclaimer, the term of this patent is extended or adjusted under 35 U.S.C. 154(b) by 0 days.

(21) Appl. No.: 15/569,897

(22) PCT Filed: Mar. 2, 2016

(86) PCT No.: PCT/KR2016/002063
§ 371 (c)(1),
(2) Date: Mar. 12, 2018

(87) PCT Pub. No.: WO2016/175441
PCT Pub. Date: Nov. 3, 2016

(65) Prior Publication Data
US 2018/0214471 A1    Aug. 2, 2018

(30) Foreign Application Priority Data
Apr. 27, 2015 (KR) .................... 10-2015-0058639

(51) Int. Cl.
*A61K 31/7048* (2006.01)
*A61K 36/815* (2006.01)
*A23L 33/105* (2016.01)
*A61P 19/10* (2006.01)

(52) U.S. Cl.
CPC ........ *A61K 31/7048* (2013.01); *A23L 33/105* (2016.08); *A61K 36/815* (2013.01); *A61P 19/10* (2018.01); *A23V 2002/00* (2013.01)

(58) Field of Classification Search
CPC ... A61K 31/7048; A61K 36/815; A61P 19/10; A23L 33/105
See application file for complete search history.

(56) References Cited

FOREIGN PATENT DOCUMENTS

| CN | 103263572 A | * | 8/2013 |
|---|---|---|---|
| KR | 10-0529544 | * | 11/2005 |
| KR | 10-1451754 | * | 10/2014 |
| KR | 101451754 B1 | | 10/2014 |
| KR | 10-2015-0016712 | * | 2/2015 |
| KR | 101524230 B1 | | 5/2015 |
| KR | 10-2015-0097874 | * | 8/2015 |
| KR | 101759725 B1 | | 8/2017 |

OTHER PUBLICATIONS

Park, E. et al., Molecules, "The Effect of Lycii Radicis Cortex Extract on Bone Formation in Vitro and in Vivo", Nov. 2014, vol. 19, 19594-19609 (Year: 2014).*
Park, E. et al., Molecules, "Effects of Dihydrophaseic Acid 3'-O-B-D-Glucopyranoside Isolated from Lycii radicis Cortex on Osteoblast Differentiation", 2016, vol. 21, pp. 1260 (Year: 2016).*
CN103263572, original patent published Aug. 2013; English machine translation, eight pages; translation obtained Nov. 14, 2019. (Year: 2013).*
Guo, S.-B. et al., Asian Journal of Chemistry, "Characterization of Hypoglycemic Constituents in *Momordica charantia* L. and their Hypoglycemic Effect", Jan. 2015, vol. 27, No. 2, pp. 393-395 (Year: 2015).*
Godevac, Dejan et al. "Chemical composition of white currant seed extract" Journal of the Serbian Chemical Society 76, No. 11 (2011): 1465-70.
Lee, Seung Young et al. "Two New Chemical Constituents from the Rhizome of Sparganium stoloniferum." Bulletin of the Korean Chemical Society 32, No. 12 (2011): 4447-9.
Ouyang, M.-A. and Kuo, Y.-H. "Water-soluble constituents from aerial roots of Ficus microcarpa." Journal of Asian Natural Products Research 8, No. 7 (2006): 625-30.
Youn, Ui Joung et al. "Identification of a New Isomer of Dihydrophaseic Acid 3'-O-β-D-Glucopyranoside from Nelumbo nucifera." Bulletin of the Korean Chemical Society 32, No. 11 (2011): 4083-5.

* cited by examiner

*Primary Examiner* — Bahar Craigo
(74) *Attorney, Agent, or Firm* — FisherBroyles, LLP

(57) ABSTRACT

The present invention relates to a compound of dihydrophaseic acid 3'-O-beta-D-glucopyranoside for the prevention and treatment of osteoporosis. It was found that the D3G isolated from the *Lycium* root bark extract induces the activity of osteoblast differentiation while promoting the proliferation of pre-osteoblast, and promotes the bone remodeling by promoting the differentiation of both osteoblast and osteoclast when mixing and culturing pre-osteoblast which is the precursor of osteoblast, and monocyte which is the precursor of osteoclast. Therefore, the D3G of the present invention is expected to be useful as a pharmacological agent or functional food effective for the prevention and treatment of osteoporosis which is a disease caused by the abnormal balance of bone remodeling.

8 Claims, 6 Drawing Sheets

[Figure 1a]
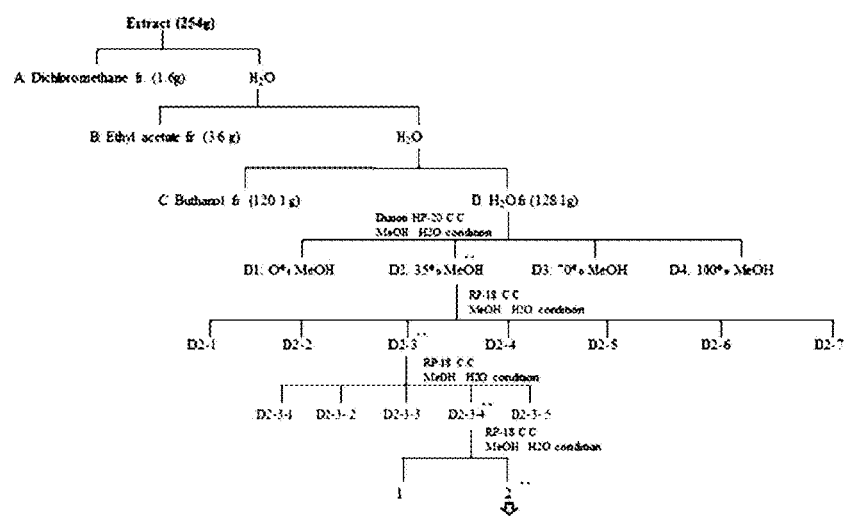
[Figure 1b]
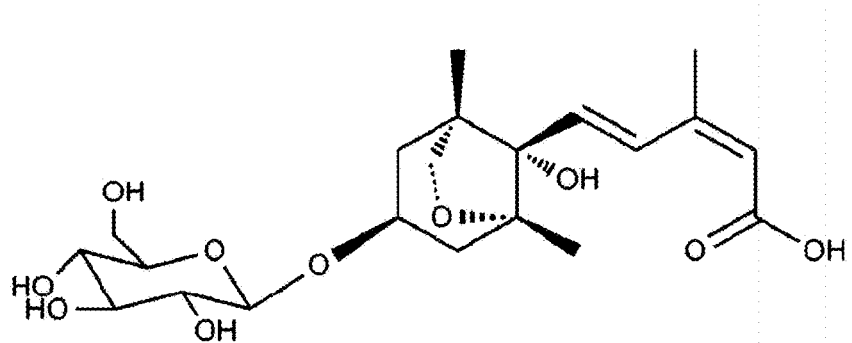

[Figure 2a]
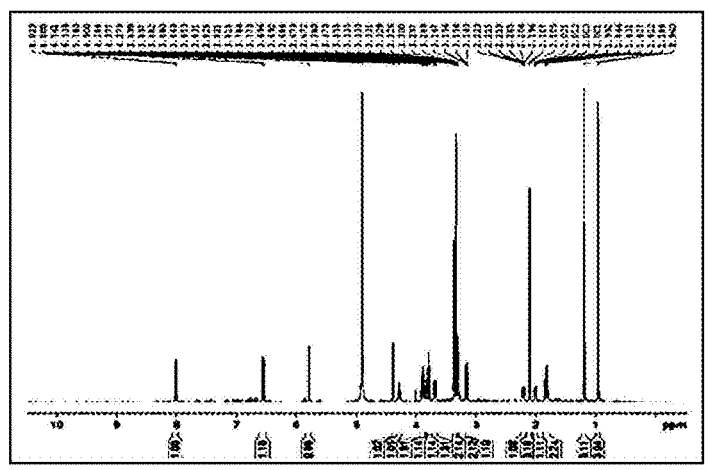
[Figure 2b]
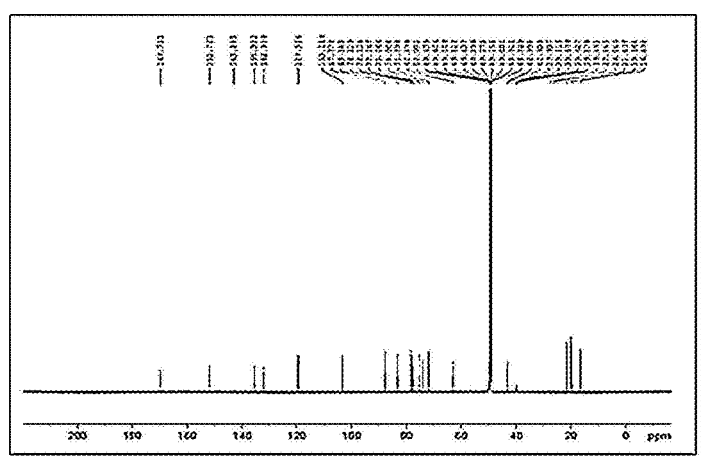
[Figure 2c]
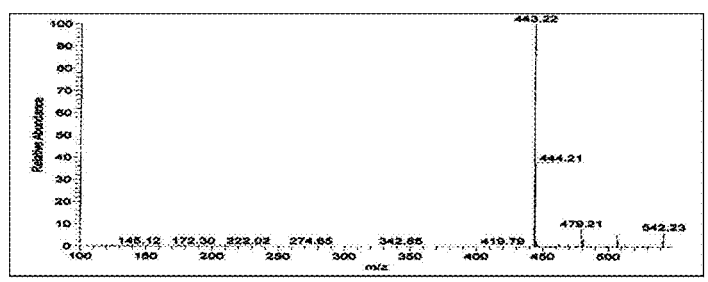

【Figure 3】
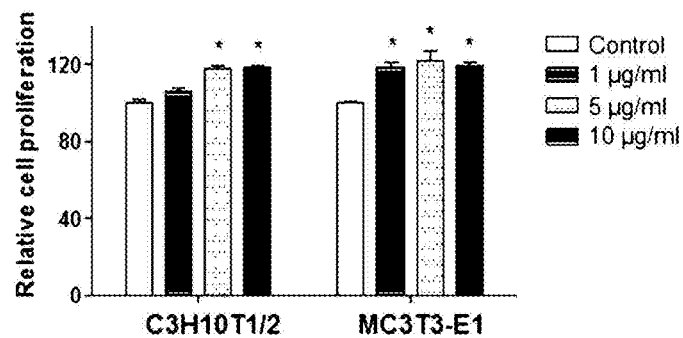
【Figure 4】
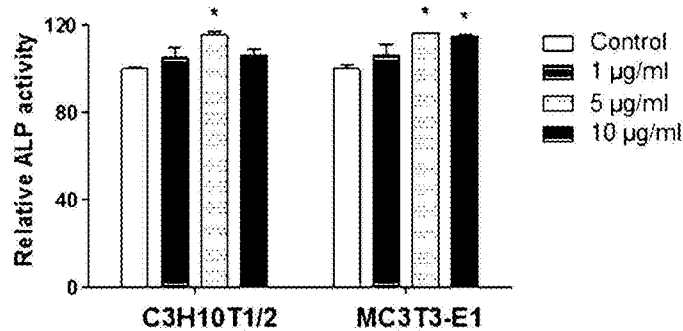
【Figure 5】
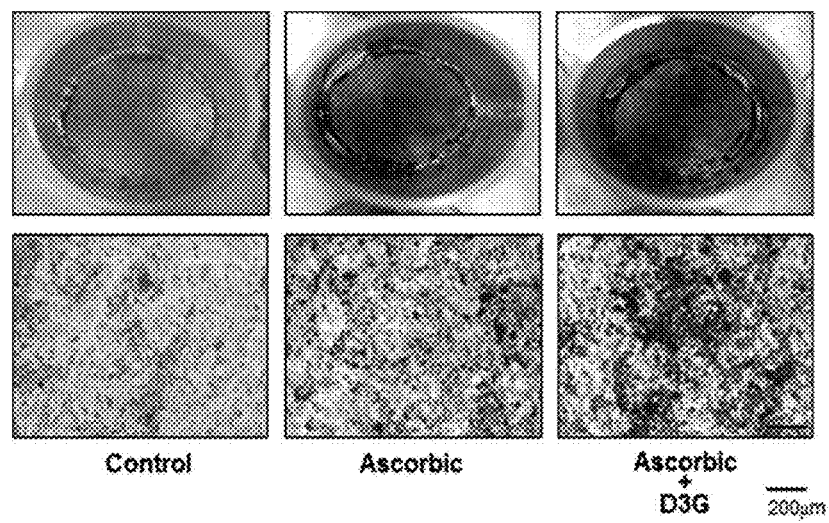

[Figure 6a]
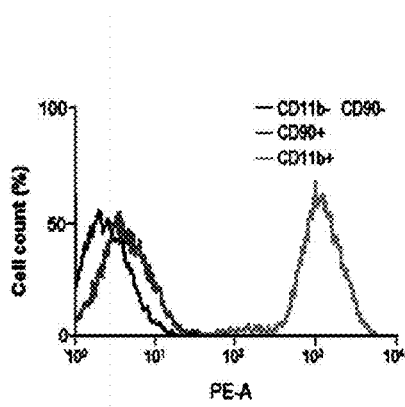
[Figure 6b]
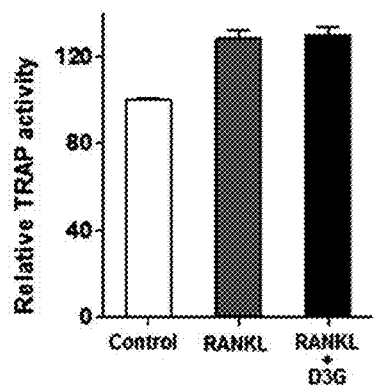
[Figure 6c]
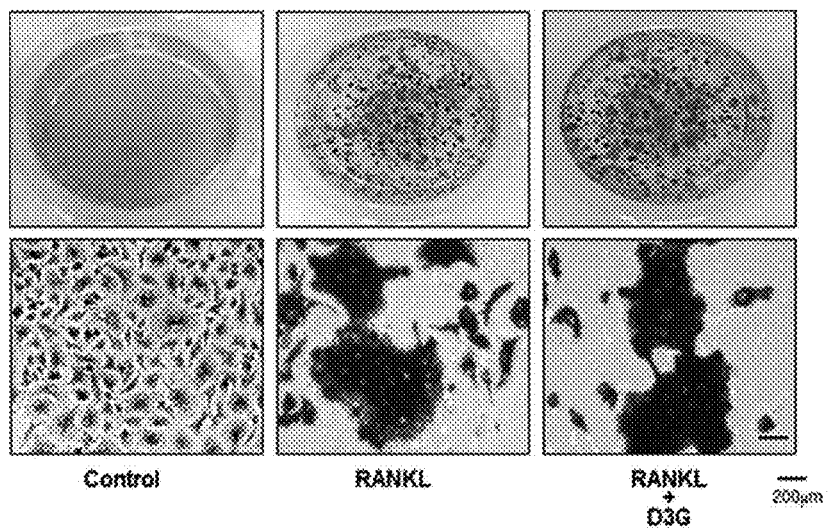

[Figure 7a]
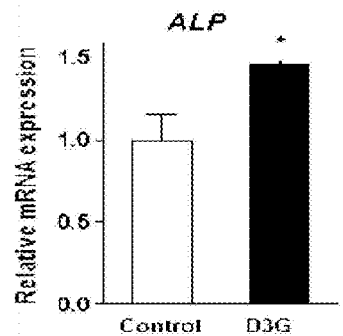
[Figure 7b]
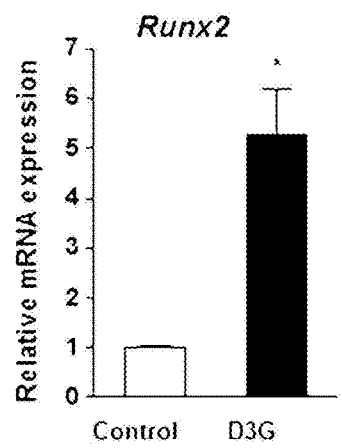
[Figure 7c]
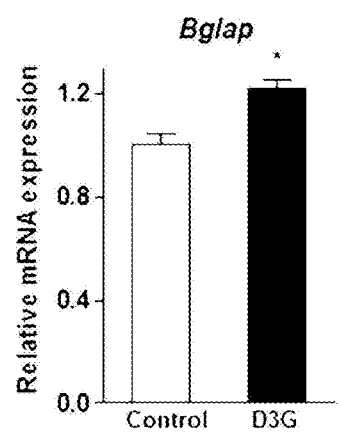

[Figure 8a]
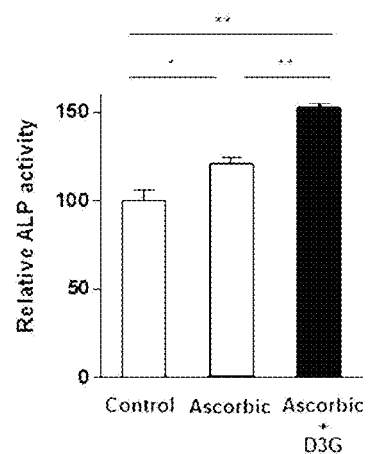
[Figure 8b]
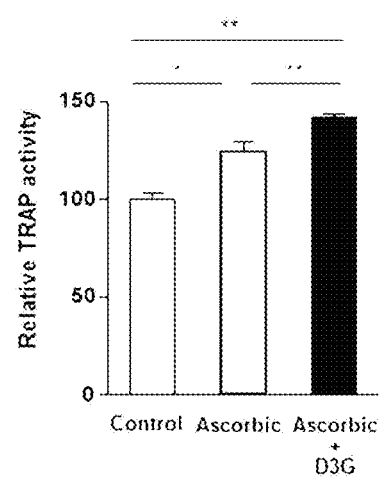

COMPOSITION FOR PREVENTING AND TREATING OSTEOPOROSIS, COMPRISING DIHYDROPHASEIC ACID 3'-O-β-D-GLUCOPYRANOSIDE ISOLATED FROM LYCIUM ROOT BARK EXTRACTS

TECHNICAL FIELD

The present invention relates to a composition for the prevention and treatment of osteoporosis comprising a compound isolated from a *Lycium* root bark extract, more particularly, to a method for isolating and identifying the compound having the prevention and treatment function of osteoporosis by promoting bone remodeling from the *Lycium* root bark extract, and to a composition for the prevention and treatment of osteoporosis including the compound.

BACKGROUND ART

Bone tissue is a dense connective tissue surrounded by osteocytes and rigid calcium tissue around the osteocytes and has the mechanical function of support and root attachment, and the bones are formed by this bone tissue to form the skeleton of the human body. In addition, the bone tissue functions to protect the bio-organ and bone marrow, and to preserve calcium and phosphorus ions to maintain homeostasis. These bone tissues are composed of several kinds of cells such as collagen, cell substrate such as glycoprotein, osteoblast, osteoclast, osteocyte and the like. Osteoblasts derived from bone marrow stromal cells play a major role in osteogenesis, and osteoclasts derived from stem cells are responsible for the absorption of the destroyed and aged bone wherein bone remodeling is maintained through a balanced action between osteogenesis and bone resorption.

When an abnormality occurs in the balance between osteoblast and osteoclast which play a major role in maintaining bone remodeling, metabolic bone diseases occur. A representative example of metabolic bone disease is osteoporosis, and osteoporosis refers to a disease that causes fractures even under a minor impact due to the increase of bone resorption activity by osteoclast compared to osteogenesis by osteoblast and consequently the decrease of total bone mass. To date, there is no effective treating method for osteoporosis and the prevention is emphasized.

The osteoblast responsible for osteogenesis is originated and formed from mesenchymal stem cell, and mineralization including calcium and the like formed by osteoblast differentiation not only maintains the strength of bone but also plays an important role in the homeostasis of calcium and hormone metabolism throughout the body. It is known that the calcium formation by differentiation of this osteoblast is regulated by vitamin D, parathyroid hormone and the like, and alkaline phosphatase (ALP), which is involved in the differentiation of osteoblast, is synthesized at the initial differentiation stage by the cross-talk of various signaling systems such as bone morphogenetic protein (BMP), Wnt, MAP kinase, calcineurin-calmodulin kinase, NF-B, AP-1, etc. in the cell, and thereafter, osteogenesis due to differentiation of osteoblast occurs by synthesizing mineralization related osteopontin, osteocalcin, type 1 collagen and the like.

Recently, efforts to produce osteoblasts in the in vitro culture conditions and to prevent or treat bone damage by enhancing the function of bone tissue using them have been increasing rapidly. It is known that osteogenic supplement and transforming growth factor beta (TGF-beta) subfamily play an important role in the formation and maintenance of bone tissue, and particularly it is reported that when BMP2 or BMP4, etc., is added to culture medium, induction of differentiation into osteoblast is increased. It is important to understand the factors and mechanisms involved in the induction of osteocyte differentiation in order to ensure materials that can perform clinically excellent function. In addition, it is very important to identify the substances that regulate these activities and use them for differentiation induction techniques.

Therefore, the inventors of the present invention have sought to find a substance that induces osteoblast differentiation activity and has an effect of improving bone density in an animal model of osteoporosis while promoting the proliferation of cell affecting to metabolism, and as a result, have confirmed that the *Lycium* root bark extract is effective in the proliferation and differentiation activity of mesenchymal stem cell and osteoblast. However, there is still insufficient research on which compounds in the *Lycium* root bark extract perform this function.

This study was supported by the High Value-added Food Technology Development Program, Ministry of Agriculture, Food and Rural Affairs, Republic of Korea (115007-3) and a National Research Foundation of Korea (NRF) grant funded by the Korean government (2013R1A1A2063201).

PRIOR ART LITERATURE

Korean Patent No. 10-1451754
Korean Laid-open Patent Publication No. 10-2015-0016712.

DISCLOSURE

Technical Problem

A technical challenge to be solved by the present invention is to provide a composition for the prevention or treatment of osteoporosis comprising a compound of dihydrophaseic acid 3'-O-β-D-glucopyranoside (hereinafter referred to as "D3G") having the function of preventing or treating osteoporosis, which is isolated from the *Lycium* root bark extract.

Technical Solution

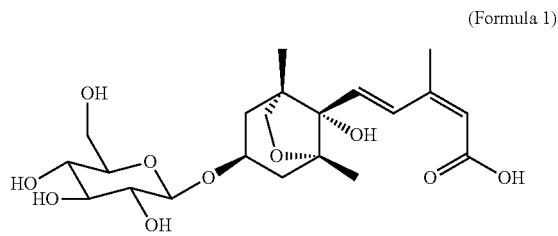 [SMILES: CC(=C/C(=O)O)/C=C/[C@]1(O)[C@]2(C)CO[C@@]1(C)C[C@@H](OC1OC(CO)C(O)C(O)C1O)C2]
(Formula 1)

In order to solve the above problem, the present invention is characterized by providing a pharmaceutical composition for the prevention and treatment of osteoporosis, which comprises dihydrophase acid 3'-O-β-D-glucopyranoside (hereinafter referred to as "D3G") represented by the formula (1) isolated from the *Lycium* root bark extract.

In addition, the present invention is characterized by providing a health functional food composition for the prevention and treatment of osteoporosis, which comprises dihydrophaseic acid 3'-O-β-D-glucopyranoside represented by the Formula (1) isolated from the *Lycium* root bark extract.

The D3G is characterized by being isolated by a method comprising, (1) obtaining a water-soluble fraction having excellent activity in the prevention and treatment of osteoporosis by suspending the *Lycium* root bark extract in water and then fractionating into organic solvent and water-soluble solvent wherein dichloromethane ethyl acetate as the organic solvent and butanol as the water-soluble solvent are used;

(2) obtaining 3 to 10 kinds of primary small fractions by performing open-column chromatography of the water-soluble fraction obtained in the above step (1) using water, methanol or a mixture of water and methanol; and (3) separating and purifying the D3G compound by performing column chromatography of the primary small fractions obtained in the above step (2).

Advantageous Effects

The D3G of the present invention has the prevention and treatment effect on osteoporosis by promoting the activity of differentiation into osteoblast while promoting the proliferation of pre-osteoblast that affect bone remodeling. Therefore, the compound of D3G (dihydrophaseic acid 3-O-β-D-glucopyranoside) of the present invention can be used as a pharmacological composition and functional food composition for the prevention and treatment of osteoporosis.

DESCRIPTION OF DRAWINGS

The following drawings attached hereto illustrate preferred embodiments of the present invention. The present invention is not limited to the matters described in the drawings, because it serves to further understand the technical idea of the present invention together with the contents of the above-mentioned invention.

FIG. 1 is a drawing showing a process of fractionating a substance efficacious for osteoblast differentiation promotion from the *Lycium* root bark extract (FIG. 1a) and the finally identified D3G structure (FIG. 1b).

FIG. 2 is a drawing showing the $^1$H-NMR spectrum (FIG. 2a), the $^{13}$C-NMR spectrum (FIG. 2b), and the mass spectrum (FIG. 2c) of D3G fractionated from the *Lycium* root bark extract.

FIG. 3 is a drawing showing the effect of cell proliferation obtained by treating C3H10T1/2 cell which is a mesenchymal stem cell and MC3T3-E1 cell which is a pre-osteoblast at concentrations of 1 μg/ml, 5 μg/ml and 10 μg/ml, respectively.

FIG. 4 is a drawing showing that the D3G has an osteoblast differentiation promotion effect, as being confirmed from the results of treating C3H10T1/2 cell which is a mesenchymal stem cell and MC3T3-E1 cell which is a pre-osteoblast with the D3G at concentrations of 1 μg/ml, 5 μg/ml and 10 μg/ml respectively, and then measuring the activity of osteoblast differentiation marker, ALP (alkaline phosphatase).

FIG. 5 is a drawing showing by alizarin red S staining that the mineralization of differentiation-inducing MC3T3-E1 cell is promoted by D3G treatment.

FIG. 6 is a drawing showing that the D3G does not affect the differentiation of osteoclast, as being confirmed from the results of treating monocyte (FIG. 6a) isolated from mouse bone marrow with D3G at an optimal concentration of 5 μg/ml and then measuring the activity of TRAP (Tartrate-resistant acid phosphatase) (FIG. 6b) which is an osteoclast differentiation marker, and TRAP staining (FIG. 6c) of differentiated osteoclast in order to measure the differentiation activity of monocyte into osteoclast FIG. 7 is a drawing showing that the D3G has an effect of promoting differentiation of osteoblast, as being confirmed from the results of treating MC3T3-E1 cell which is a pre-osteoblast with D3G and then quantitatively analyzing gene expression levels of osteogenesis-related gene markers, Alp (FIG. 7a), Runx2 (FIG. 7b) and Bglap (FIG. 7c) by real-time PCR method FIG. 8 is a drawing showing that the D3G promotes differentiation of both osteoblasts and osteoclast, as being confirmed from the results of mixing and culturing MC3T3-E1 cell, which is a pre-osteoblast, and monocyte, which is differentiated into osteoclast, and then measuring the activity of ALP (alkaline phosphatase) (FIG. 8a) and the activity of TRAP (Tartrate-resistant acid phosphatase) (FIG. 8b), in order to test the effect of the D3G under the most similar condition to the in vivo environment.

BEST MODE

The present invention relates to the D3G isolated and purified by fractionation from the *Lycium* root bark extract, and to a pharmaceutical composition comprising the same for the prevention and treatment of osteoporosis.

Hereinafter, the constitution of the present invention will be described in detail.

The D3G of the present invention is produced by obtaining a water-soluble fraction having excellent activity in the prevention and treatment of osteoporosis by suspending the *Lycium* root bark extract in water and then fractionating into the organic solvent and water-soluble solvent wherein dichloromethane ethyl acetate as the organic solvent and butanol as the water-soluble solvent are used; obtaining 3 to 10 kinds of primary small fractions by performing open-column chromatography of the water-soluble fraction obtained in the above step (1) using water, methanol or a mixture of water and methanol; and separating and purifying the D3G compound by performing column chromatography of the primary small fractions obtained in the above step (2).

The D3G of the present invention, which is a component isolated from *Lycium* root barks, has not yet been reported in bone-related articles or patents. Since the D3G is a compound that cannot be purchased, the evaluation test for the in vitro efficacy in osteogenesis and bone resorption was performed using the fraction layer containing the D3G among fractions of the *Lycium* root bark extract.

In the present invention, the bone remodeling activity of the D3G fraction layer fractionated and extracted from the *Lycium* root bark was measured, and specifically, the in vitro experiment was performed by treating C3H10T1/2 cell line as a mesenchymal stem cell and MC3T3-E1 cell line as a pre-osteoblast, which are mainly used for bone remodeling studies, with the *Lycium* root bark extract. The mesenchymal stem cell refers to a cell with differentiation ability to osteoblast or adipocyte, and the pre-osteoblast refers to a cell at a stage prior to differentiation into osteoblast. The effect of the D3G on cell proliferation was investigated in these two cell lines, the degree of activity of alkaline phosphatase (ALP) was examined to confirm the effectiveness of differentiation activity, and the change pattern of osteoblast differentiation gene markers was examined to confirm the effectiveness of osteoblast differentiation at the molecular level. In addition, the differentiation activity of osteoclast was investigated by measurement of TRAP (Tartrate-resistant acid phosphatase) activity. In order to investigate the effect of the D3G under the most similar condition to the in vivo environment, the effect of the D3G on bone remodeling was analyzed by mixing and culturing MC3T3-E1 cell which is a pre-osteoblast and monocyte which is differentiated into osteoclast.

In the present invention, it has been proved that the D3G promotes the activity of ALP, an osteoblast differentiation marker and increases the expression level of osteoblast differentiation gene markers, and the D3G has the effect of promoting the differentiation of osteoblast and osteoclast, that is, promoting bone remodeling, when mixing and culturing pre-osteoblast and monocyte.

Hereinafter, in order to facilitate understanding of the present invention, embodiments and the like will be described in detail. However, the embodiments according to the present invention can be modified into various other forms, and the scope of the present invention should not be construed as being limited to the following embodiments. Embodiments of the present invention are provided to more fully describe the present invention to those skilled in the art.

Example 1: Preparation of *Lycium* Root Bark Extract

After purchasing the *Lycium* root bark and before using it as a test substance, the suitability as a test substance was confirmed by Pharmaceutical Quality Team of Dong-Duang Pharmaceutical Co., Ltd. in Korea through close examination based on Korean Pharmacopoeia, residual sulfur dioxide analysis, residual heavy metal measurement, residual pesticide analysis and the like.

1.0 kg of the *Lycium* root bark was washed and dried in hot air at 60° C. After grinding to 60 mesh or less, 3.3 L of water and 7.7 L of ethanol were added and extracted at 80° C. for 4 hours to prepare a *Lycium* root bark extract.

Then, the *Lycium* root bark extract was centrifuged at 15,000 rpm for 15 minutes, and then concentrated under reduced pressure at about 70° C. until the water content became about 30% or less. After filtration, the concentration process was again carried out to obtain a concentrated *Lycium* root bark extract.

Example 2: Isolation and Identification of D3G From *Lycium* Root Bark Extract 254 g of the *Lycium* root bark extract was suspended in distilled water, followed by solvent fractionation with dichloromethane ethyl acetate and butanol. Each fraction layer was evaporated under reduced pressure to obtain individual solvent extracts, and the activity of each extract was assayed. As a result of the activity assay, since the activity of the water layer was excellent, the water layer was subjected to open column chromatography using Daion HP-20. As a result of the experiment, a total of four small fractions were obtained, which were fractionated with water, 35% aqueous methanol solution, 70% aqueous methanol solution and 100% methanol. As a result of the activity assay, the fraction of 35% aqueous methanol solution (D2 fraction) showed good activity, and thus this fraction was subjected to RP-18 column chromatography to obtain a total of 7 fractions. D2-3 fractions showing activity were isolated and purified to obtain a single compound (FIG. 1a). The isolated and purified compound was identified as dihydrophaseic acid 3-O-b-D-glucopyranoside (D3G) by comparing the results of analysis with 1D and 2D NMR data analyzed using 700 MHz NMR (cryo probe), LC-MS data and the existing literature (FIG. 2a-c).

Experimental Example 1: Culture of Cell

C3H10T1/2 cells which are mouse mesenchymal stem cells and MC3T3-E1 cells which are pre-osteoblasts were cultured in Basal Medium Eagle (BME) medium supplemented with 10% fetal bovine serum, 1 mM sodium pyruvate, 100 units/L penicillin and 100 mg/L streptomycin and α-minimal essential medium (α-MEM) at 37° C. under 5% $CO_2$.

In the case of MC3T3-E1 cells, ascorbic acid (50 µg/ml) and β-Glycerophosphate (10 mM), which are the osteoblast differentiation-inducing agents, were added, and then differentiation was induced for 3 days before treatment with the D3G fraction layer.

The D3G fraction layer obtained in Examples 1 and 2 was dissolved in sterilized distilled water and divided into three groups of concentrations of 1 µg/ml, 5 µg/ml and 10 µg/ml, and then added them to C3H10T1/2 cells and MC3T3-E1 cells respectively and further cultured for 48 hours. Cells cultured in the absence of the D3G fraction layer were used as a control.

Osteoclasts was isolated from primary monocytes, which are the myoblasts of osteoclasts from the bone marrow of a 6 week old mouse, and cultured them. After confirming that the osteoclasts isolated from mouse stem cells were monocytes isolated from the bone marrow of the mouse through FACS (FIG. 6a) (monocyte positive marker antibody: CD11b), an experiment was performed. Separated mouse monocytes were treated with 30 ng/ml M-CSF and 50 ng/ml LANKL, which are osteoclast differentiation-inducing agents, and differentiation was induced for 3 days before treatment with D3G fraction layer.

Experimental Example 2: Cell Proliferation Assay

Cell proliferation assays were performed using a EZ-Cytox Enhanced Cell Viability Assay Kit product with water-soluble tetrazolium salt.

Specifically, C3H10T1/2 cells and MC3T3-E1 cells ($3 \times 10^3$ cells/well) were inoculated into 96-well plates and cultured in growth medium at 37° C. for 24 hours in 5% $CO_2$, and then the *Lycium* root bark extracts of three concentrations (1 µg/ml, 5 µg/ml and 10 µg/ml) were added to the cells and cultured for 2 days. Tetrazolium salt was added to each cultured cell and sample, and cultured at 37° C. for 2 hours. The absorbance was measured at 450 nm, and the reference wavelength was 655 nm, and the results are shown in FIG. 3.

Statistical analysis was performed by student's t-test for the control group without extract treatment and for each treatment group with extract treatment, and expressed as *$p<0.05$ depending on significance level.

As shown in FIG. 3, it was confirmed that when treating with the D3G fraction layer at individual concentrations, the proliferation of C3H10T1/2 cells of mesenchymal stem cells and MC3T3-E1 cells of pre-osteoblasts promotes cell proliferation at various concentrations.

As a result of the analysis of cell proliferation for the D3G fraction layer in the C3H10T1/2 cells and differentiation induced MC3T3-E1 cells according to the method as described above, it was shown that in both cell lines used in the experiment, the D3G fraction layer promotes cell proliferation, and specifically it was analyzed that the cell proliferation promoting effect, when treating at the optimal concentration of 5 µg/mL of the D3G, was the highest.

Experimental Example 3: Analysis of ALP Activity

After culturing the D3G-treated experimental group treated with the three kinds of concentrations (1 µg/ml, 5 µg/ml, 10 µg/ml) and the control group for 48 hours, ALP activity of cells was measured. ALP activity was measured using a ALP Assay Kit.

Specifically, after washing the cells with the physiological saline, the cell lysed with cytolytic agent was treated with p-nitrophenyl phosphate which is a substrate of ALP and then cultured at 37° C. for 1 hour. Thereafter, 0.5N NaOH which is a reaction stop solution was added, and then the absorbance was measured at a wavelength of 405 nm.

The effect of the cell ALP activity of the *Lycium* root bark extract in C3H10T1/2 cells and differentiation induced MC3T3-E1 cells was analyzed by the method as described above, and the results are shown in FIG. 4. Statistical analysis was performed by Student's t-test, and was expressed as *p<0.05, depending on the significance level.

As shown in FIG. 4, it was confirmed that C3H10T1/2 cells, which are mesenchymal stem cells, and MC3T3-E1 cells, which are pre-osteoblasts, increase ALP activity, when treating with the D3G, and the best effect was obtained in the treatment group of 5 µg/mL.

From these results, it was found that in both cell lines used in the experiments, the cell ALP activity is enhanced by D3G treatment. Especially, it was analyzed that at the concentration of 5 µg/ml of the *Lycium* root bark extract, the enhancing effect of cell ALP activity was the best.

Experimental Example 4: Analysis of Mineralization Action

The analysis of mineralization action of the cells was performed after incubation of the experimental group treated with 5 µg/ml of the D3G and the control group for 3 weeks. The analysis of mineralization action was performed using the Alizarlin red S staining method.

As shown in FIG. 5, it was confirmed that MC3T3-E1 cells which are pre-osteoblasts when treating with the D3G increase mineralization in the 5 µg/mL treated group.

From these results, it was found that when treating with the D3G in the experiment, the MC3T3-E1 cell lines which are pre-osteoblasts improve mineralization action.

Experimental Example 5: Osteoclast Differentiation

Osteoclasts are derived from stem cells and are responsible for bone resorption that destroys aged bone wherein bone remodeling is maintained through the balanced action of osteogenesis by osteoblasts and bone resorption by osteoclasts. To the monocytes extracted and cultured from the stem cells of the femoral region of the mouse, 30 ng/mL M-CSF and 50 ng/mL RANKL were added together and then cultured for 5 days. Thereafter, the activity of TRAP which is an osteoclast differentiation marker was measured.

After washing the cells with physiological saline, TRAP activity was measured by absorbance at a wavelength of 405 nm using an Acid-Phosphatase Kit, and after staining, the osteoclasts were observed through a microscope.

As shown in FIG. 6a, the monocytes which are maternal cells of osteoclasts were well isolated by the stem cells isolated from the femoral region of the mouse.

As shown in FIGS. 6b and 6c, the isolated monocytes were differentiated by osteoclast inducers, but there was no significant change between D3G treated and untreated groups.

These results suggest that the D3G treatment does not affect osteoclast differentiation.

Experimental Example 6: Analysis of Expression Level of Osteoblast Differentiation Gene Marker The change in the expression levels of mRNAs of osteoblast differentiation gene markers, Alp, Runx2, and Bglap (Osteocalcine) among bone remodeling-related gene markers was confirmed by a quantitative reverse transcription-PCR.

After harvesting the cells, total RNA was isolated using Trizol, and in order to remove genomic DNA, DNase I was reacted at room temperature for 15 minutes and then treated with EDTA to inactivate DNase I.

Thereafter, the reverse transcription reaction was induced by using oligo dT primer as a primer to synthesize cDNA, and then real-time PCR was performed using sequence specific primers of each gene and SYBR Green. The analysis of the expression level was performed by using the relative quantification method for the target gene using the Gapdh gene as a control. The gene-specific primer sequence information for identifying the level of expression of the gene markers used to determine the degree of differentiation of osteoblasts and osteoclasts is shown in Table 1 below.

TABLE 1

| Kind | Gene | Sequence name | Sequence information (5->3) |
|---|---|---|---|
| Control | Gapdh | Gapdh-F | TGA CCA CAG TCC ATG CCA TC (SEQ ID NO: 1) |
| | | Gapdh-R | GAC GGA CAC ATT GGG GGT AG (SEQ ID NO: 2) |
| Osteoblast differentiation gene marker | Alp | Alp-F | TCC CAC GTT TTC ACA TTC GG (SEQ ID NO: 3) |
| | | Alp-R | CCC GTT ACC ATA TAG GAT GGC C (SEQ ID NO: 4) |
| | Runx2 | Runx2-F | TAA AGT GAC AGT GGA CGG TCC C (SEQ ID NO: 5) |
| | | Runx2-R | TGC GCC CTA AAT CAC TGA GG (SEQ ID NO: 6) |
| | Bglap (Osteo calcin) | Bglap-F | TAG TGA ACA GAC TCC GGC GCT A (SEQ ID NO: 7) |
| | | Bglap-R | TGT AGG CGG TCT TCA AGC CAT (SEQ ID NO: 8) |

Expression levels of the three gene markers, Alp, Runx2, and Bglap related to bone remodeling for the D3G in differentiation-induced MC3T3-E1 cells were compared by the method as described above, and the results are shown in FIGS. 7a, 7b, and 7c. Statistical analysis was performed by student's t-test and expressed as *p<0.05 depending on significance level. The treatment concentration of the D3G was at the concentration of 5 µg/ml which was the most effective in cell proliferation and ALP activity test. As shown in FIGS. 7a, 7b, and 7c, the expression levels of the three gene markers, Alp, Runx2, and Bglap treated with the D3G were all increased in the MC3T3-E1 cell lines.

Experimental Example 7: Mixed Culture of Osteoblast and Osteoclast

In order to assess the maintenance of bone remodeling under the condition closer to the in vivo condition through the balanced action between osteogenesis and bone resorption by osteoblasts and osteoclasts, MC3T3-E1($2\times10^4$ cells/well), which are pre-osteoblasts, and monocytes ($4\times10^4$ cells/well) obtained by extracting stem cells from the femoral region of the mouse and culturing them were mixed and cultured.

To the mixed culture of osteoblasts and osteoclasts, ascorbic acid (50 μg/ml) and β-glycerophosphate (10 mM) which are osteoblast differentiation-inducing agents were added to induce differentiation for 3 days and then treated with D3G fraction layer. After adding the D3G fraction layer (5 μg/mL) to the mixed culture solution, the activity of ALP which is an osteoblast differentiation marker and the activity of TRAP which is an osteoclast differentiation marker were measured. Statistical analysis was performed by student's t-test and expressed as *$p<0.05$ and **$p<0.01$ depending on significance level.

As shown in FIGS. 8a and 8b, Mixed and cultured cells were confirmed to increase both ALP and TRAP activity when treating with D3G treatment. These results showed a significant increase in both osteoblast differentiation and osteoclast differentiation in the mixed culture. Taken together with the results of the experiments described above, it is considered that the D3G promotes bone turnover, i.e., bone remodeling.

The D3G according to the present invention induces the osteoblast differentiation activity while promoting the proliferation of the pre-osteoblasts that affect the bone remodeling promotion and the D3G has bone remodeling effect by inducing not only osteoblast but also osteoclast differentiation in the mixed culture of the pre-osteoblasts and the monocytes. Therefore, the D3G of the present invention is expected to be useful as a pharmacological agent or a functional food for the prevention and treatment of osteoporosis.

The invention claimed is:
1. A method of preventing or treating osteoporosis comprising administering to a person in need thereof a composition of isolated dihydrophaseic acid 3'-O-β-D-glucopyranoside represented by the following formula (1) isolated from a *Lycium* root bark extract:

(Formula 1)

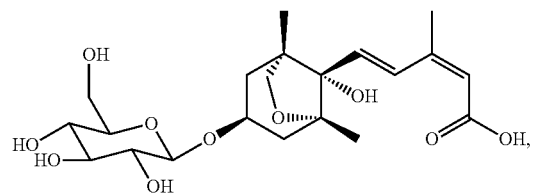

wherein the dihydrophaseic acid 3'-O-β-D-glucopyranoside is isolated by a method comprising,
(1) obtaining a water-soluble fraction having activity in the prevention and treatment of osteoporosis by suspending the *Lycium* root bark extract in water and then fractionating into organic solvent and water-soluble solvent;
(2) obtaining 3 to 10 fractions by performing open-column chromatography of the water-soluble fraction obtained in the above step (1) using water, methanol or a mixture of water and methanol; and
(3) separating and purifying the dihydrophaseic acid 3'-O-β-D-glucopyranoside compound by performing additional column chromatography of the fractions obtained in the above step (2).

2. The method of claim 1, wherein the organic solvent is dichloromethane and ethyl acetate, and the water-soluble solvent is butanol.

3. A method of preventing or treating osteoporosis comprising administering to a person in need thereof a composition consisting of isolated dihydrophaseic acid 3'-O-β-D-glucopyranoside represented by the following formula (1) isolated from a *Lycium* root bark extract:

(Formula 1)

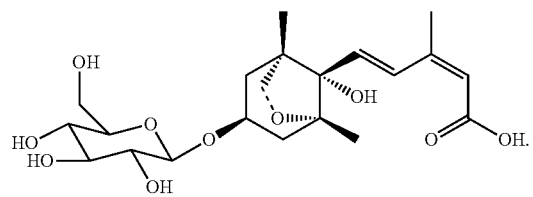

4. The method of claim 1, wherein the composition is in a pharmaceutical formulation.
5. The method of claim 1, wherein the composition is in a food formulation.
6. The method of claim 3, wherein the composition is in a pharmaceutical formulation.
7. The method of claim 3, wherein the composition is in a food formulation.
8. A method of treating osteoporosis comprising administering to a person in need thereof a composition of isolated dihydrophaseic acid 3'-O-β-D-glucopyranoside represented by the following formula (1) isolated from a *Lycium* root bark extract:

(Formula 1)

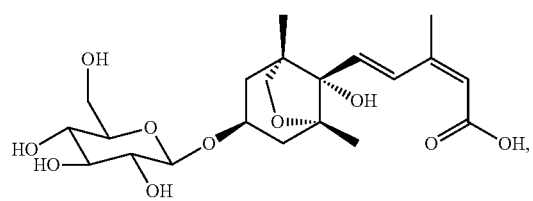

wherein the dihydrophaseic acid 3'-O-β-D-glucopyranoside is isolated by a method comprising,
(1) obtaining a water-soluble fraction having activity in the prevention and treatment of osteoporosis by suspending the *Lycium* root bark extract in water and then fractionating into organic solvent and water-soluble solvent;
(2) obtaining 3 to 10 fractions by performing open-column chromatography of the water-soluble fraction obtained in the above step (1) using water, methanol or a mixture of water and methanol; and
(3) separating and purifying the dihydrophaseic acid 3'-O-β-D-glucopyranoside compound by performing additional column chromatography of the fractions obtained in the above step (2).

* * * * *